(12) United States Patent
Moreno Frias et al.

(10) Patent No.: US 9,527,920 B2
(45) Date of Patent: Dec. 27, 2016

(54) RECOMBINANT ANTIBODIES HAVING DUAL SPECIFICITY FOR GANGLIOSIDES AND USE THEREOF

(71) Applicant: CENTRO DE INMUNOLOGIA MOLECULAR, La Habana (CU)

(72) Inventors: Ernesto Moreno Frias, La Habana (CU); Gertrudis Rojas Dorantes, La Habana (CU); Ana Victoria Casadesus Pazos, La Habana (CU)

(73) Assignee: CENTRO DE IMMUNOLOGIA MOLECULAR, La Habana (CU)

( * ) Notice: Subject to any disclaimer, the term of this patent is extended or adjusted under 35 U.S.C. 154(b) by 0 days.

(21) Appl. No.: 14/379,628

(22) PCT Filed: Feb. 21, 2013

(86) PCT No.: PCT/CU2013/000001
§ 371 (c)(1),
(2) Date: Aug. 19, 2014

(87) PCT Pub. No.: WO2013/127373
PCT Pub. Date: Sep. 6, 2013

(65) Prior Publication Data
US 2015/0093385 A1 Apr. 2, 2015

(30) Foreign Application Priority Data

Mar. 1, 2012 (CU) .................. CU/P/2012-0035

(51) Int. Cl.
*A61K 39/395* (2006.01)
*C07K 16/30* (2006.01)
*A61K 39/00* (2006.01)

(52) U.S. Cl.
CPC ..... *C07K 16/3084* (2013.01); *A61K 2039/505* (2013.01); *C07K 2317/33* (2013.01); *C07K 2317/565* (2013.01)

(58) Field of Classification Search
None
See application file for complete search history.

(56) References Cited

U.S. PATENT DOCUMENTS

2015/0093385 A1* 4/2015 Moreno Frias et al. ... 424/136.1

FOREIGN PATENT DOCUMENTS

EP 1623997 * 8/2006

OTHER PUBLICATIONS

Watarai et al J. Biochem. vol. 117 p. 062 (1995).*
Paul, Fundamental Immunology, 3rd Edition, 1993, pp. 292-295.*
Rudikoff et al(Proc. Natl. Acad. Sci. USA 1982 vol. 79: p. 1979).*
Pascalis et al (The Journal of Immunology (2002) 169, 3076-3084).*
Casset et al. (2003) BBRC 307, 198-205.*
Rojas et al ACS Chemical Biology vol. 8 p. 376 (2013).*
Azuma et al., Recombinant Human Hexamer-Dominant IgM Monoclonal Antibody to Ganglioside GM3 for Treatment of Melanoma,Clin Cancer Res 13:2745-50, 2007.
Bada et al., Toxicity of a GM3 cancer vaccine in Macaca fascicularis monkey: a 12-month study, Exp Toxicol. 21:263-7, 2002.
Blanco et al., Immunoreactivity of the 14F7 Mab Raised against N-Glycolyl GM3 Ganglioside in Epithelial Tumors from Digestive System, ISRN Gastroenterol, Article ID 645641, 2011.
Blanco et al., Immunorecognition of the 14F7 Mab Raised against N-Glycolyl GM3 Ganglioside in Some Normal and Malignant Tissues from Genitourinary System, ISRN Pathology, Article ID 953803, 2011.
Boffey et al., Characterisation of the immunoglobulin variable region gene usage encoding the murine anti-ganglioside antibody repertoire, J Neuroimmunol 165:92-103, 2005.
Bostrom et al., Variants of the Antibody Herceptin That Interact with HER2 and VEGF at the Antigen Binding Site, Science 323:1610-14, 2009.
Carr et al., A mouse IgG1 Monoclonal Antibody Specific for N-Glycolyl GM3 Ganglioside Recognized Breast and Melanoma Tumors, Hybridoma 19:241-47, 2000.
Carr et al., In Vivo and In Vitro Anti-Tumor Effect of 14F7 Monoclonal Antibody, Hybridoma 21:463-8, 2002.
Catimel et al., Direct immobilization of gangliosides onto gold-carboxymethyldextran sensor surfaces by hydrophobic interaction: applications to antibody characterization; Glycobiology, 1998 8(9):927-938.
Cheever et al., The Prioritization of Cancer Antigens: A National Cancer Institute Pilot Project for the Acceleration of Translational Research, Clinical Cancer Res 15: 5323-37, 2009.
Dohi et al., An IgG3 Monoclonal Antibody Established after Immunization with G M3 Lactone: Immunochemical Specificity and Inhibition of Melanoma Cell Growth in Vitro and in Vivo, Cancer Res 48, 5680-5, 1988.
Fernández et al., NGcGM3 Ganglioside: A Privileged Target for Cancer Vaccines, Clin Devel Immunol, Article ID 814397, 2010.
Fernández et al., Ganglioside-based vaccines and anti-idiotype antibodies for active immunotherapy against cancer, Expert Rev Vaccines 2:817-23, 2003.
Fernandez-Marrero et al., Switching on cytotoxicity by a single mutation at the heavy chain variable region of an anti-ganglioside antibody, Mol Immunol 48:1059-67, 2011.
Guthmann et al., Active Specific Immunotherapy of Melanoma with a GM3 Ganglioside-Based Vaccine, J Immunother 27:242-51, 2004.
Hakomori, Glycosylation defining cancer malignancy: New wine in an old bottle, PNAS USA 99: 10231-10233, 2002.

(Continued)

*Primary Examiner* — Sheela J Huff
(74) *Attorney, Agent, or Firm* — Rothwell, Figg, Ernst & Manbeck, P.C.

(57) ABSTRACT

The present invention relates to new monoclonal antibodies and fragments of these antibodies, which have dual specificity and high affinity for N-acetyl GM3 and N-glycolyl GM3 and do not recognize other gangliosides. In another aspect, the present invention relates to the use of these antibodies and their fragments in the therapy of tumors characterized by a significant expression of any of the two antigens recognized by these antibodies, or a mixed expression of both antigens. Likewise, the invention relates to the use of these antibodies in the diagnosis of tumors expressing at least one of the two variants of the GM3 ganglioside.

20 Claims, 3 Drawing Sheets

(56) References Cited

OTHER PUBLICATIONS

Hernández et al., Anti-NeuGcGM3 Antibodies, Actively Elicited by Idiotypic Vaccination in Nonsmall Cell Lung Cancer Patients, Induce Tumor Cell Death by an Oncosis-Like Mechanism, J Immunol 186:3735-44, 2011.
Hersey et al., Expression of the gangliosides GM3, GD3 and GD2 in tissue sections of normal skin, naevi primary and metastatic melanoma, Int. J. Cancer, 1988 41(3):336-343.
Hirabayashi et al., Syngeneic Monoclonal Antibody against Melanoma Antigen with Interspecies Cross-reactivity Recognizes GM3, a Prominent Ganglioside of B16 Melanoma, J Biol Chem 260:13328-33, 1985.
Hollander, Bispecific antibodies for cancer therapy, Immunotherapy 1:211-22, 2009.
Hoogenboom, Overview of antibody phage-display technology and its applications, Methods in Molecular Biology 2002 178():1-37.
Hoon et al., Molecular Cloning of a Human Monoclonal Antibody Reactive to Ganglioside GM3 Antigen on Human Cancers, Cancer Res 53:5244-20, 1993.
Hu et al., Reducing Epitope Spread during Affinity Maturation of an Anti-Ganglioside GD2 Antibody, J Immunol 183: 5748-55, 2009.
Hudson and Souriau, Engineered antibodies, Nat Med 9:129-34, 2003.
Irie et al., Phase 1 pilot clinical trial of human IgM monoclonal antibody to ganglioside GM3 in patients with metastatic melanoma, Cancer Immunol Immunother 53:110-7, 2004.
Kotani et al., Generation of one set of monoclonal antibodies specific for a-pathway ganglio-series gangliosides, Biochimica et Biohysica Acta, 1117:97-103, 1992.
Krengel et al., Structure and Molecular Interactions of a Unique Antitumor Antibody Specific for N-Glycolyl Gm3*, The Journal of Biological Chemistry, 279:5597-603, 2004.
Lee et al., Phage-Display Selection of a Human Single-Chain Fv Antibody Highly Specific for Melanoma and Breast Cancer Cells Using a Chemoenzymatically Synthesized Gm3-Carbohydrate Antigen, J. Am. Chem. Soc. 124:12439-46, 2002.
Livingston et al., Antibody response after immunizationwith the gangliosides GM1, GM2, GM3, GD2 and GD3 in the mouse, Cancer Immunol Immunother 29:179-84, 1989.
Marquina et al., Gangliosides Expressed in Human Breast Cancer, Cancer Res 56:5165-71, 1996.
Moreno et al., Delineation of the epitope recognized by an antibody specific for N-glycolylneuraminic acid-containing gangliosides, Glycobiology 8; 695-708, 1998.
Roque-Navarro et al., Anit-ganglioside antibody-induced tumor cell death by loss of membrane integrity, Mol Cancer Ther 7 (7):2033-41, 2008.
Nishinaka et al., Human IgM antibodies to tumor-associated gangliosides share VHIII (V3-23) and VKIV family subgroups, Immunogenetics 48:73-5, 1998.
Noguchi et al., Endogenously produced ganglioside GM3 endows etoposide and doxorubicin resistance by up-regulating Bcl-2 expression in 3LL Lewis lung carcinoma cells, Glycobiology 16:641-50, 2006.
Oliva et al., Clinical evidence of GM3 (NeuGc) ganglioside expression in human breast cancer using the 14F7 monoclonal antibody labelled with 99mTc, Breast Cancer Research and Treatment 96:115-21, 2006.
Portoukalian, Immunogenity of Glycolipids, Clinical Reviews in Allergy and Immunology, 19:73-78, 2000.

Prokazova et al., Ganglioside GM3 and Its Biological Funcitons, Biochemistry (Moscow) 74:235-49, 2009.
Ravindranath et al., Immunogenic gangliosides in human ovarian carcinoma, Biochemical and Biophysical Research Communications, 353:251-8, 2007.
Rojas et al., Light-chain shuffling results in successful phage display selection of functional prokaryotic-expressed antibody fragments to N-glycolyl GM3 ganglioside, Journal of Immunological Methods; 293:71-83, 2004.
Scursoni et al., Detection of N-Glycololyl GM3 Ganglioside in Neuroectodermal Tumors by Immunohistochemistry: An Attractive Vaccine Target for Aggressive Pediatric Cancer, Clinical and Development Immunology, Article ID 245181, 2011.
Svennerholm et al., Gangliosides and Synaptic Transmission, Structure and Function of Ganglioside, 125:533-540, 1980.
Townson et al., Solid phase immunoadsorption for therapeutic and analytical studies on neuropathy-associated anti-GM1 antibodies, Glycobiology 17:294-303, 2007.
Varki, N-glycolylneuraminic acid deficiency in humans, Biochimie 83:615-22, 2001.
Vaquez et al., Generation of a Murine Monoclonal Antibody Specific for N-Glycolyneuraminic Acid-Containing Gangliosides That Also Recognizes Sulfated Glycolipids, Hybridoma 14:551-56, 1995.
Yamaguchi et al., Cell-surface antigens of melanoma recognized by human monoclonal antibodies, Proc. Natl. Acad. Sci. USA, 84:2416-20, 1987.
Mukerjee et al., Characterization of Human IgG1 Monoclonal Antibody Against Gangliosides Expressed on Tumor, Cells, Hybridoma, 17(2):133-142, 1998.
Watarai s et al: II Production of Monoclonal Antibodies Directed to Hanganutziu-Deicher Active Gangliosides. N-Glycolylneuraminic Acid-Containing Gangliosides11, Journal of Biochemistry. Japanese Biochemical Society I OUP Tokyo; JP, vol. 117. No. 5. Jan. 1, 1995 (Jan. 1, 1995). pp. 1062-1069. XP008049192. ISSN: 0021-924X table 3.
Hoon D S et al: 11 Molecular Cloning of a Human Monoclonal Antibody Reactive to Ganglioside GM3 Antigen on Huamn Cancers11 • Cancer Research. American Association for Cancer Research. US. vol. 53. No. 21. Nov. 1, 1993 (Nov. 1, 1993). pp. 5244-5250. XP002017118. ISSN: 0008-5472 table 3.
Rojas Gertrud!S et al: 11 Engineering the Binding Site of an Antibody against N-Glycolyl GM3: From Functional Mapping to Novel Anti-ganglioside Specificities. ACS Chemical Biology. American Chemical Society. Washington. DC. US. vol. 8. No. 2. Feb. 1, 2013 (Feb. 1, 2013). pp. 376-386. XP009171240. ISSN: 1554-8929. DOI: 10.1021/CB30037541 the whole document.
U. Krengel: 11 Structure and Molecular Interactions of a Unique Antitumor Antibody Specific for N-Glycolyl GM311 Journal of Biological Chemistry. vol. 279. No. 7. Dec. 15, 2003 (Dec. 15, 2003). pp. 5597-5603. XP55071570. ISSN: 0021-9258. DOI: 10.1074/jbc.M311693200 the whole document.
Rojas G et al: 11 Light-chain shuffling results in successful phage display selection of functional prokaryotic-expressed antibody fragments to N-glycolyl GM3 ganglioside. Journal of Immunological Methods. Elsevier Science Publishers B.V.Amsterdam. NL. vol. 293. No. 1-2. Oct. 1, 2004 (Oct. 1, 2004). pp. 71-83. XP004634276. ISSN: 0022-1759. DOI: 10.1016/J.JIM.2004.07.002 the whole document.
International Search Report in PCT/CU2013/00001, dated Aug. 30, 2013, 5 pages.

* cited by examiner

| Cell line | Percent of cell death (PI incorporation) | | | |
|---|---|---|---|---|
| | Non-treated cells | T1h (isotype control) | 14F7hT | 7C1 |
| L1210 | 13 | 6 | 50 | 95 |
| L1210-SH | 9 | 10 | 13 | 54 |

RECOMBINANT ANTIBODIES HAVING DUAL SPECIFICITY FOR GANGLIOSIDES AND USE THEREOF

CROSS REFERENCE TO RELATED APPLICATION

This application is a 35 U.S.C. 371 National Phase Entry Application from PCT/CU2013/000001, filed Feb. 21, 2013, which claims the benefit of Cuban Patent Application No. CU/P/2012-0035 filed on Mar. 1, 2012, the disclosures of which are incorporated herein in their entirety by reference.

TECHNICAL FIELD

The present invention relates to the field of biotechnology and in particular to human health. This invention provides monoclonal antibodies which have been modified by genetic engineering and describes the use of these antibodies and their fragments for the therapy and/or diagnosis of tumors.

PRIOR ART

The N-Acetyl GM3 and N-Glycolyl GM3 Gangliosides as Tumor-Associated Antigens

Gangliosides are sialic acid-containing glycosphingolipids that are found in the plasma membranes of vertebrates. These molecules are involved in different functions such as cellular adhesion, signal transduction, tissue development and differentiation, and also in tumor progression (Hakomori, PNAS USA 99:225-32, 2002).

Several gangliosides have been characterized as tumor-associated antigens because they are expressed, or have an increased expression in certain types of cancer. N-glycolyl GM3 (NeuGc-GM3) and N-acetyl GM3 (NeuAc-GM3, or simply GM3) are tumor-associated antigens.

The present invention relates to monoclonal antibodies that bind with high affinity to both N-glycolyl GM3 and N-acetyl GM3.

NeuGc-GM3 is not expressed in normal human tissues (Varki, Biochimie 83:615-22, 2001), but it is found in several types of tumors (Marquina et al., Cancer Res 56:5165-71, 1996; Fernández et al., Expert Rev Vaccines 2:817-23, 2003).

Although N-acetyl GM3 is common in normal human tissues (Svennerholm, in Structure and Function of Gangliosides, Plenum Press, New York-London, pp. 533-540, 1980; Prokazova et al., Biochemistry (Moscow) 74:235-49, 2009), it has been defined as a tumor-associated antigen because it is over-expressed in different types of cancers (Hersey et al., Int J Cancer 41:336-43, 1988; Ravindranath et al., Biochem Biophys Res Commun 353:251-8, 2007; Noguchi et al., Glycobiology 16:641-50, 2006). In a recent study coordinated by the US National Cancer Institute, which was aimed to define which antigens should be prioritized as targets for cancer immunotherapy, GM3 occupied the 48$^{th}$ position among the 75 antigens that resulted selected in the study (Cheever et al., Clinical Cancer Res 15: 5323-37, 2009).

The N-acetyl GM3 and N-glycolyl GM3 gangliosides have very similar structures. They are composed of three monosaccharide units (sialic acid, galactose and glucose) and a ceramide tail. The two gangliosides differ from each other only because of the enzymatic hydroxylation of the methyl group present in the nitrogen function of N-acetyl sialic acid (NeuAc), which is converted this way into N-glycolyl sialic acid (NeuGc). In other words, NeuAc- and NeuGc-GM3 differ from each other only because of the substitution of a hydroxyl group for a hydrogen atom in their sialic acid unit. This small structural difference, however, results in a marked different recognition by the immune system (Portoukalian, Clin Rev Allergy Immunol 19:73-78, 2000; Varki, Biochimie 83: 615-22, 2001).

Monoclonal Antibodies that Recognize the N-Acetyl GM3

Several monoclonal antibodies of murine or human origin that recognize GM3 (N-acetyl) have been described in the literature: M2590 mAb (murine IgM) (Hirabayashi et al., J Biol Chem 260:13328-33, 1985); FCM1 mAb (human IgM) (Yamaguchi et al., PNAS 84:2416-20, 1987); DH2 mAb (murine IgG) (Dohi et al., Cancer Res 48, 5680-5, 1988); GMR6 mAb (murine IgM) (Kotani et al., Biochim Biophys Acta 1117:97-103, 1992); L612 mAb (human IgM) (Hoon et al., Cancer Res 53:5244-20, 1993); mAbs "17" and AH18 (human IgM) (Brandt et al., U.S. Pat. No. 5,610,280A, 1997); GMA1 mAb (human IgG) (Mukerjee et al., Hybridoma 17:133-42, 1998). From these eight antibodies, mAbs DH2 and L612 have been shown to be specific for GM3, whereas the other six antibodies show extended reactivity towards other gangliosides. None of these antibodies has been shown to recognize neither N-glycolyl GM3 nor other N-glycolylated gangliosides.

In a more recent report, three anti-GM3 antibodies (called GM3A6, GM3A8 and GM3A15) were obtained from a phage display library of single-chain Fv (scFv) fragments. This library was constructed from the antibody gene repertoires of a group of cancer patients (Lee et al., J Am Chem Soc 124:12439-46, 2002). The dissociation constants (KD) of these fragments, as determined by SPR/Biacore, were in the order of $10^{-5}$-$10^{-7}$ M.

In general, the affinities of anti-ganglioside monoclonal antibodies have been found to be within a low/medium range. The dissociation constants measured by SPR/Biacore for the Fab fragments of several of these antibodies are in the order of $10^{-6}$-$10^{-7}$ M (Catimel et al., Glycobiology 8:927-38; Boffey et al., J Neuroimmunol 165:92-103, 2005; Townson et al., Glycobiology 17:294-303, 2007) with only a few exceptions, as for example, anti-GD2 and anti-GD1b fragments showing KDs in the order of $10^{-8}$ M (Boffey et al., J Neuroimmunol 165:92-103, 2005; Hu et al., J Immunol: 183; 5748-55, 2009).

For N-acetyl GM3 in particular, its low immunogenicity represents a serious obstacle to obtain high affinity IgG antibodies (Livingston et al., Cancer Immunol Immunother 29:179-84, 1989; Portoukalian, Clin Rev Allergy Immunol 19:73-8, 2000).

Preclinical and Clinical Results with Anti-N-Acetyl GM3 Antibodies

Evidences of in vitro and in vivo anti-tumor activity have been published for mAbs DH2 and L612. mAb DH2 induced antibody-dependent cellular toxicity in vitro and inhibited the growth of B16 melanoma cells in C57BL/6 mice (Dohi et al., Cancer Res 48, 5680-5, 1988). mAb L612 produced complement-dependent cytotoxicity in in vitro experiments with cancer cells expressing N-acetyl GM3 (Nishinaka et al., J Immunogenetics 48:73-5, 1998). An engineered version of this antibody, displaying a hexameric IgM format, showed increased capabilities of producing complement-dependent cellular death and a greater anti-tumor effect in mice (Azuma et al., Clin Cancer Res 13:2745-50, 2007).

mAb L612 has been used in the clinic in a phase I trial that involved nine patients with metastatic melanoma (Inci et al., Cancer Immunol Immunother 53:110-7, 2004). At present, this is the only clinical trial of an anti-N-acetyl GM3 antibody that has been reported. Several patients showed clinical responses to the treatment. Furthermore, the antibody did not produce toxic effects in spite of the ubiquity of N-acetyl GM3 in normal tissues.

The N-acetyl GM3 ganglioside has been also the target of active immunotherapy in the clinic, namely in a phase I trial of the GM3/VSSP vaccine in melanoma patients (Guthmann et al., J Immunother 27:242-51, 2004). Previously, in experiments performed during 12 months in monkeys, this vaccine generated a strong anti-GM3 antibody response of both IgM and IgG isotypes, without producing toxic effects (Bada et al., Exp Toxicol. 21:263-7, 2002). In the clinical trial, the anti-N-acetyl GM3 antibodies generated in patients were of IgM isotype. No toxic effects of consideration were observed.

Monoclonal Antibodies that Recognize the N-Glycolyl GM3

Two monoclonal antibodies that recognize N-glycolyl GM3, but not its N-acetylated variant, have been described in the literature: mAb P3 (murine IgM) (Vazquez et al., Hybridoma 14:551-56, 1995) and mAb 14F7 (murine IgG) (Carr et al., Hybridoma 19:241-47, 2000). The P3 antibody recognizes also other N-glycolylated gangliosides (Moreno et al., Glycobiology 8, 695-708, 1998), whereas the 14F7 antibody is specific for N-glycolyl GM3.

The conceptual design and genetic engineering of the antibodies that are the subject of the present invention are based on the amino acid sequences and the crystal structure of the variable domains of the 14F7 antibody (Krengel et al., J Biol Chem 279:5597-603, 2004).

The 14F7 Monoclonal Antibody

The monoclonal antibody 14F7, produced by the hybridoma deposited under the accession code ECACC 98101901, has been described in the patent application EP 0972782/A1. Humanized variants and fragments of this antibody are described in the patent application WO 2004/094477/A1.

mAb 14F7 is an IgG immunoglobulin that recognizes N-glycolyl GM3 with high specificity (Carr et al., Hybridoma 19:241-47, 2000) and high affinity, showing a dissociation constant in the order of $10^{-8}$ M, as measured for its Fv fragment (Rojas et al., J Immunol Methods 293:71-83, 2004) Immunohistochemical studies have shown that 14F7 recognizes several types of tumors, such as ductal breast carcinoma and melanoma (Carr et al., Hybridoma 19:241-47, 2000), adenocarcinomas of the stomach, colon and pancreas (Blanco et al., ISRN Gastroenterol, Article ID 645641, 2011), tumors of the genitourinary system (Blanco et al., ISRN Pathology, Article ID 953803, 2011) and neuroectodermal tumors (Scursoni et al., Clin Devel Immunol, Article ID 245181, 2011).

The N-glycolyl GM3 binding site of 14F7 is located in the variable domain of its heavy chain (VH), as demonstrated through the construction of a phage display library of scFv fragments that combine the VH domain of mAb 14F7 with a large variety of light chain variable domains of both murine and human origin (Rojas et al., J Immunol Methods 293:71-83, 2004). More than one third of the library fragments were capable of recognizing the N-glycolyl GM3, which furthermore demonstrates that the VH domain of mAb 14F7 can be paired with different light chain variable domains (VL) while maintaining the original antibody specificity.

In in vitro and in vivo studies, mAb 14F7 was capable of producing complement-independent cellular death and inhibiting the growth of myelomas in mice (Carr et al., Hybridoma 21:463-8, 2002). In a prospective phase I/II clinical trial carried out in breast cancer patients, the technetium-labeled 14F7 antibody accumulated in tumors (Oliva et al., Breast Cancer Res Treat 96:115-21, 2006).

More recent studies showed that 14F7 kills tumor cells, but not normal cells, through a novel mechanism that produces lesions in the cellular membrane (Roque-Navarro et al., Mol Cancer Ther 7:2033-41, 2008). The high affinity of mAb 14F7 constitutes a key factor to produce this kind of death, as shown in recent experiments using a mutant of mAb P3 with increased affinity (Fernandez-Marrero et al., Mol Immunol 48:1059-67, 2011). Neither mAb P3 nor its chimeric version P3Q were able to induce complement-independent cell death in tumor cells expressing N-glycolyl GM3, whereas the mutant obtained by Fernandez-Marrero and coworkers (called P3Q E99R), which shows an increased affinity for N-glycolyl GM3 (in-between the affinities of mAbs P3Q and 14F7), was capable of producing this type of cell death. It should be noted that mAb 14F7, having a higher affinity, showed a stronger effect of complement-independent cell death as compared to that produced by the P3 E99R mutant.

Therapies in the Clinic Targeting the N-Glycolyl GM3

At present, the strongest evidences showing that antibodies against N-glycolyl GM3 may have anti-tumor effects come from the phase II/III clinical trials of two molecular vaccines targeting this ganglioside. One of these products is the NGcGM3/VSSP vaccine, which contains the N-glycolyl GM3 molecule in its formulation. The second product is an anti-idiotypic antibody called Racotumumab or 1E10 (Fernández et al., Clin Devel Immunol, Article ID 814397, 2010). Both vaccines induce high anti-N-glycolyl GM3 antibody titers in cancer patients, with clearly demonstrated anti-tumor effects (Fernandez et al., Clin Devel Immunol, Article ID 814397, 2010; Hernandez et al., J Immunol 186:3735-44, 2011).

Phage Display Libraries of Antibody Fragments

The dual-specificity antibodies that are the subject of this invention were obtained from a phage display library of scFv fragments, which was specifically designed with this objective. Phage display of antibody fragments is a high-throughput technology that allows the construction of libraries containing a large number of fragments (up to billions) with different amino acid sequences, and the subsequent selection of those fragments having the desired properties in terms of specificity and affinity (Hoogenboom, Methods Mol Biol 178:1-37, 2002).

Antibodies with Dual Specificity

Cancer is a disease characterized by genetic heterogeneity, which makes it very difficult to treat using a single therapeutic agent. For this reason, combinatorial therapies targeting different cancer-associated antigens may have a higher success probability. A possible approach in this direction is to combine antibodies with different specificities. This kind of therapy, however, would be very expensive due to the high costs of developing and producing each of the antibodies.

Using genetic engineering, it has been possible to create a variety of methods to obtain antibodies, or antibody fragments having the capability of recognizing two or more molecules. The most common method consists in combining more than one antibody binding region, each of them having a different specificity, into a single molecular construction (Hudson and Souriau, Nat Med 9:129-34, 2003; Hollander, Immunotherapy 1:211-22, 2009). Recently, a new conceptual design of antibodies showing dual specificity has been described. In this new approach, the binding site of a monoclonal antibody is engineered for recognition of a second antigen, while keeping the recognition of the original antigen. This new design was applied to the antibody Herceptin by using the phage display technology. As result, a mutant was obtained which not only keeps the high affinity binding to the original antigen (the HER2 molecule), but recognizes also the vascular endothelial growth factor (VEGF) with high affinity (Bostrom et al., Science 323: 1610-14, 2009). This new conceptual design of an antibody with dual specificity ("two-in-one" antibody) has several advantages. One of them—a very important advantage—is that dual-specificity antibodies can be easily produced as monoclonal antibodies.

DETAILED DESCRIPTION OF THE INVENTION

The present invention relates to recombinant monoclonal antibodies with dual specificity and high affinity for the N-acetyl GM3 and N-glycolyl GM3 gangliosides. The invention includes also within its scope any fragments derived from these antibodies.

In a preferred embodiment, the present invention relates to antibodies with dual specificity and high affinity for the N-acetyl GM3 and N-glycolyl GM3 gangliosides, characterized in that the heavy chain variable region of said antibodies contains the following CDRs:

```
CDR-H1
                              SEQ ID NO: 3
GYRFRSYQIH,

CDR-H2
                              SEQ ID NO: 17
YIDPATAYTESNQKFKD,

CDR-H3
                              SEQ ID NO: 34
ESPRLRRGIYYYAMDY,
```

In another preferred embodiment the invention relates to antibodies characterized in that the sequence of the heavy chain variable region is SEQ ID NO: 1:

```
QVQLQQSGNELAKPGASMKMSCRASGYRFRSYQIHWLKQRPDQGLEWIGY

IDPATAYTESNQKFKDKAILTADRSSNTAFMYLNSLTSEDSAVYYCARES

PRLRRGIYYYAMDYWGQGTSVTVSS
```

In another particular embodiment, the invention relates to monoclonal antibodies characterized in that the heavy chain variable region has the sequence seq. with ID number 1:

```
QVQLQQSGNELAKPGASMKMSCRASGYRFRSYQIHWLKQRPDQGLEWIGY

IDPATAYTESNQKFKDKAILTADRSSNTAFMYLNSLTSEDSAVYYCARES

PRLRRGIYYYAMDYWGQGTSVTVSS
``` and the light chain variable region has the sequence seq. with ID number 2:

```
DLVLTQSPATLSVTPGDSVSFSCRASQSISNNLHWYQQRTHESPRLLIKY

ASQSISGIPSRFSGSGSGTDFTLSIISVETEDFGMYFCQQSNRWPLTFGA

GTKLELKRA
```

In another aspect, the invention relates to a monoclonal antibody characterized in that the sequence of the heavy chain variable region is seq. with ID number 1:

```
QVQLQQSGNELAKPGASMKMSCRASGYRFRSYQIHWLKQRPDQGLEWIGY

IDPATAYTESNQKFKDKAILTADRSSNTAFMYLNSLTSEDSAVYYCARES

PRLRRGIYYYAMDYWGQGTSVTVSS
``` whereas the sequence of the light chain variable region is any sequence of light chain variable region of an antibody.

In another aspect, the light chain variable region is any light chain variable region of a human antibody.

In another particular aspect, the light chain variable region is any light chain variable region of a humanized antibody.

In a preferred embodiment, the present invention relates to an antibody characterized in that the heavy chain binding domain comprises a CDR-H1 sequence selected from a group consisting of the following sequences:

```
CDR-H1
                              SEQ ID NO: 3
GYRFRSYQIH,

CDR-H1
                              SEQ ID NO: 4
GYSFTRYQIH,

CDR-H1
                              SEQ ID NO: 5
GYRFTSNQIH,

CDR-H1
                              SEQ ID NO: 6
GYSFNRYQIH,

CDR-H1
                              SEQ ID NO: 7
GYSFRRYQIH,

CDR-H1
                              SEQ ID NO: 8
GYSITRYQIH,

CDR-H1
                              SEQ ID NO: 9
GYSFTRYQIH,

CDR-H1
                              SEQ ID NO: 10
GYSFKSYQIH,

CDR-H1
                              SEQ ID NO: 11
GYSFTSYQIH,

CDR-H1
                              SEQ ID NO: 12
GYRFTRYWIH,

CDR-H1
                              SEQ ID NO: 13
GYTFTRYQIH,

CDR-H1
                              SEQ ID NO: 14
GYPFTRYQIH,

CDR-H1
                              SEQ ID NO: 15
GYSFSRYQIV,

CDR-H1
                              SEQ ID NO: 16
GYHFTRYQIH,
```

In another embodiment, the antibodies of the present invention are characterized in that the sequence of CDR-H2 is selected from a group consisting of the following sequences:

CDR-H2
YIDPATAYTESNQKFKD, SEQ ID NO: 17

CDR-H2
YINPATASTESNQKFKD, SEQ ID NO: 18

CDR-H2
FIDPATAYTESNQKFKD, SEQ ID NO: 19

CDR-H2
DIDPGRAYTESNQKFKD, SEQ ID NO: 20

CDR-H2
YIDPATANTESNQKFKD, SEQ ID NO: 21

CDR-H2
FINPATAYTESNQKFKD, SEQ ID NO: 22

CDR-H2
FIDPASAYTVSNQKFKD, SEQ ID NO: 23

CDR-H2
YIDPATAKTESNQKFKD, SEQ ID NO: 24

CDR-H2
YINPGSAYTESNQKFKD, SEQ ID NO: 25

CDR-H2
YLDPANAYTESNQKFKD, SEQ ID NO: 26

CDR-H2
YVDPANAYTESNQKFKD, SEQ ID NO: 27

CDR-H2
YINPATAYTESNQKFKD, SEQ ID NO: 28

CDR-H2
YIDPATAWTESNQKFKD, SEQ ID NO: 29

CDR-H2
YIDPGTAYTESNQKFKD, SEQ ID NO: 30

CDR-H2
YIDPRTAYTESNQKFKD, SEQ ID NO: 31

CDR-H2
YVDPATAHTESNQKFKD, SEQ ID NO: 32

CDR-H2
YINPATAYTDSNQKFKD, SEQ ID NO: 33

In an additional embodiment, the antibodies of the present invention are characterized in that the sequence of CDR-H3 is selected from a group consisting of the following sequences:

CDR-H3 . . .
ESPRLRRGIYYYAMDY, SEQ ID NO: 34

CDR-H3 . . .
ESPRFRRGRYYYAMDY, SEQ ID NO: 35

CDR-H3 . . .
ESPRMRRGIYYYAMDY, SEQ ID NO: 36

CDR-H3 . . .
ESPRVRRGIYYYAMDY, SEQ ID NO: 37

CDR-H3 . . .
ESPRLRRGLYYYAMDY, SEQ ID NO: 38

In another embodiment, the antibodies of the present invention comprise any combination of the sequences of CDRs H1, H2 and H3 that have been listed above.

In another embodiment, the antibodies of the present invention are characterized in that the sequence of CDR-H2 and/or the sequence of CDR-H3 comprise at least one of the amino acid substitutions selected from the group that consist of:
  CDR-H2 Asp 52 substituted by Ala, Glu, Asn, Ser or Thr
  CDR-H2 Ala 53 substituted by Asp, Glu, Gly, His, Leu, Ser, Thr or Tyr
  CDR-H3 Arg 100-Arg 100A substituted by Ala-Lys, His-Arg or Thr-Arg
  CDR-H3 Gly 100B substituted by Ala, Asp, Phe, Leu, Gln, Arg or Ser
  CDR-H3 Tyr 100 D substituted by Phe
and additionally comprises any light chain from an antibody.

In another particular embodiment, the antibodies of the invention comprise the human IgG1 heavy chain constant region and the human kappa light chain constant region.

In another aspect, the invention relates to the Fab, Fab', (Fab)2 and scFv fragments of the antibodies of the present description.

The fragments of the present invention are characterized by:
a CDR-H1 sequence that is selected from a group consisting of the following sequences:

CDR-H1
GYRFRSYQIH, SEQ ID NO: 3

CDR-H1
GYSFTRYQIH, SEQ ID NO: 4

CDR-H1
GYRFTSNQIH, SEQ ID NO: 5

CDR-H1
GYSFNRYQIH, SEQ ID NO: 6

CDR-H1
GYSFRRYQIH, SEQ ID NO: 7

CDR-H1
GYSITRYQIH, SEQ ID NO: 8

CDR-H1
GYSFTRYQIH, SEQ ID NO: 9

CDR-H1
GYSFKSYQIH,                SEQ ID NO: 10

CDR-H1
GYSFTSYQIH,                SEQ ID NO: 11

CDR-H1
GYRFTRYWIH,                SEQ ID NO: 12

CDR-H1
GYTFTRYQIH,                SEQ ID NO: 13

CDR-H1
GYPFTRYQIH,                SEQ ID NO: 14

CDR-H1
GYSFSRYQIV,                SEQ ID NO: 15

CDR-H1
GYHFTRYQIH,                SEQ ID NO: 16 a CDR-H2 sequence that is selected from a group consisting of the following sequences:

CDR-H2
YIDPATAYTESNQKFKD,         SEQ ID NO: 17

CDR-H2
YINPATASTESNQKFKD,         SEQ ID NO: 18

CDR-H2
FIDPATAYTESNQKFKD,         SEQ ID NO: 19

CDR-H2
DIDPGRAYTESNQKFKD,         SEQ ID NO: 20

CDR-H2
YIDPATANTESNQKFKD,         SEQ ID NO: 21

CDR-H2
FINPATAYTESNQKFKD,         SEQ ID NO: 22

CDR-H2
FIDPASAYTVSNQKFKD,         SEQ ID NO: 23

CDR-H2
YIDPATAKTESNQKFKD,         SEQ ID NO: 24

CDR-H2
YINPGSAYTESNQKFKD,         SEQ ID NO: 25

CDR-H2
YLDPANAYTESNQKFKD,         SEQ ID NO: 26

CDR-H2
YVDPANAYTESNQKFKD,         SEQ ID NO: 27

CDR-H2
YINPATAYTESNQKFKD,         SEQ ID NO: 28

CDR-H2
YIDPATAWTESNQKFKD,         SEQ ID NO: 29

CDR-H2
YIDPGTAYTESNQKFKD,         SEQ ID NO: 30

CDR-H2
YIDPRTAYTESNQKFKD,         SEQ ID NO: 31

CDR-H2
YVDPATAHTESNQKFKD,         SEQ ID NO: 32

CDR-H2
YINPATAYTDSNQKFKD,         SEQ ID NO: 33 a CDR-H3 sequence that is selected from a group consisting of the following sequences:

CDR-H3 . . .
ESPRLRRGIYYYAMDY,          SEQ ID NO: 34

CDR-H3 . . .
ESPRFRRGRYYYAMDY,          SEQ ID NO: 35

CDR-H3 . . .
ESPRMRRGIYYYAMDY,          SEQ ID NO: 36

CDR-H3 . . .
ESPRVRRGIYYYAMDY,          SEQ ID NO: 37

CDR-H3 . . .
ESPRLRRGLYYYAMDY,          SEQ ID NO: 38

In another embodiment, the fragments of the present invention comprise any combination of the sequences of CDRs H1, H2 and H3 that have been listed above.

These antibodies and their fragments are useful for the diagnostic and therapeutic purposes that are exposed in the present description. Therefore, in another aspect the present invention relates to compositions that comprise the antibodies of the present description, and/or fragments of these antibodies, for the diagnosis or treatment of diseases related to the ganglioside antigens N-acetyl GM3 and N-glycolyl GM3.

Preferably, the present invention comprises compositions, including pharmaceutical compositions, that contain one or several antibodies, or fragments derived from these antibodies, with dual specificity and high affinity for the N-acetyl GM3 and N-glycolyl GM3 gangliosides. Even preferably, the invention comprises pharmaceutical compositions that contain at least one antibody and/or fragment of the present invention and a pharmaceutically acceptable vehicle and/or adjuvant. Even more preferably, the present invention comprises an antibody containing a heavy chain variable region with SEQ ID NO: 1 and a light chain variable region with SEQ ID NO: 2.

In one aspect, the present invention relates also to methods of treatment that comprise the antibodies of the invention and fragments derived from these antibodies, for subjects with tumor expressing at least one of the N-acetyl GM3 or N-glycolyl GM3 ganglioside antigens.

In a particular embodiment, the subject is a human being.

In an additional aspect, the invention relates to a kit of reagents that is useful for tumor diagnosis, which comprises at least one of the antibodies of the invention and/or fragments derived from these antibodies. In a preferred embodiment, the use of this kit of reagents comprises, but is not limited to the diagnosis based on, for example, the presence of N-acetyl GM3 and/or N-glycolyl GM3 in a tissue sample or a fluid from the patient, for example, a tumor tissue sample, a blood sample, etc.

Method for Obtaining the Antibodies of the Invention

Design and Construction of a Phage Display Library of scFv Fragments, Based on mAb 14F7

The antibodies and antibody fragments of the present invention were obtained from a phage display library of single-chain Fv (scFv) antibody fragments, especially designed with this purpose in mind. The novelty and rationale of this library design reside, in the first place, in the careful selection of the positions to be randomized in the scFv amino acid sequence, which were restricted to a region with high probability of being involved in antigen binding.

In the present description, the Kabat numbering scheme is used to number the amino acid sequence of the VH antibody domain. For the antibody and fragments that are subject of the present invention, this numbering scheme introduces insertion letters after positions 52 (52A), 82 (82A, 82B, 82C) and 100 (from 100A to 100H).

The light chain variable domain (VL) of a scFv fragment called 3Fm, obtained in a previous work (Rojas et al., J Immunol Methods 293:71-83, 2004), was chosen as the only VL domain used to construct the scFv library. The 3Fm scFv fragment contains the VH domain of 14F7 mAb, whereas its VL domain was extracted from a library of murine light chains and therefore is not related to the original VL domain of 14F7 mAb. Nonetheless, the 3Fm fragment maintained the specificity and high affinity for N-glycolyl GM3 shown by mAb 14F7, in spite of the marked differences between their light chains Importantly, the 3Fm fragment could be expressed in bacteria.

Taking into account the experimental data obtained by Rojas et al. (J Immunol Methods 293:71-83, 2004) and Krengel et al. (J Biol Chem 279:5597-603, 2004), which indicate that the light chain is not important for antigen recognition, the sequence of the VL domain was kept invariant in the library.

The VH sequence of mAb 14F7 was taken as the base sequence to design the VH domains of the scFv library. The selection of the group of positions to be mutated, all of them located in the VH hyper variable loops, was based on the analysis of the crystal structure of the 14F7 Fab fragment (Krengel et al., J Biol Chem 279:5597-603, 2004) and the data showing that only the VH domain is critical for NeuGc-GM3 binding. The selection of the positions to be mutated was based on two main criteria: 1) Mutations should be made preferably for amino acids whose side chains are exposed to the solvent; and 2) the positions to be mutated were circumscribed to a region within a radius of 12 angstroms from position 52 in VH. This last criterion was based on mutagenesis experiments reported by Krengel et al. (J Biol Chem 279:5597-603, 2004), which show that amino acid Asp 52 is involved in the interaction of 14F7 mAb with its antigen.

In total, twenty positions in the VH binding site were subjected to soft randomization (Fairbrother et al., Biochemistry 37:17754-64, 1998) by adjusting the process of gene synthesis of the VH domain. Using this soft randomization procedure, it was possible to introduce any of the twenty natural amino acids in each of the selected variable positions while keeping at the same time, in each individual molecule, a limited degree of divergence from the original VH sequence of mAb 14F7.

The following positions were subjected to randomization: Ser 28, Phe 29, Thr 30, Ser 31, Trp 33, Ile 34, Tyr 50, Ile 51, Asp 52, Ala 53, Thr 54, Tyr 56, Glu 58, Arg 98, Leu 99, Arg 100, Arg 100A, Gly 100B, Ile 100C and Tyr 100D.

Three of the positions subjected to mutation, Phe 29, Ile 34 and Ile 51, correspond to hydrophobic amino acids which have their side chains buried in the protein and which are important to keep the conformations of CDRs H1 and H2. For these three amino acids in particular, as well as for Leu 99 in CDR H3, especially designed codons were used: T̲T̲T̲, A̲TT, A̲TT and T̲TG̲, respectively, where underlined nucleotides represent the mixture of that nucleotide (85%) with an equimolar mixture of the other three nucleotides (15%). These partially degenerated codons code for hydrophobic amino acids, favoring the insertion of the original amino acid the corresponding positions. The purpose behind this design was to generate a limited diversity, which would have only small effects on CDR conformation while possibly having some modulation effects on the binding affinity.

Taking into account that Krengel and coworkers (Krengel et al., J Biol Chem 279:5597-603, 2004) demonstrated that amino acid Asp 52 is important for binding of 14F7 to NeuGc-GM3, a particular mixture of codons was designed for this position (G-80%/A-20%)A̲(C-50%/T-50%), coding for six different amino acids having mostly small and medium size side chains, and among which the original aspartic acid predominates. For the remaining 15 randomized positions, each base of the triplet coding for a given position was synthesized using a mixture containing 85% of the original nucleotide and 15% of an equimolar mixture of the other three nucleotides.

The designed VH gene collection was synthesized and cloned into the pHAB phagemid vector, containing the gene coding for the 3Fm scFv fragment (Rojas et al., J Immunol Methods 293:71-83, 2004). The phages presenting the scFv fragments were rescued from the library using the M13 K07 auxiliary bacteriophage, and were subsequently purified using the procedure described by Marks and coworkers (J Mol Biol 222:581-97, 1991).

The obtention of mutant scFv fragments having the capability of recognizing with high affinity the N-acetyl GM3 ganglioside, while keeping at the same time the high affinity recognition of N-glycolyl GM3, was no doubt a surprising result. Indeed, the amino acid changes in the VH domain of mAb 14F7 that conferred the new properties to these mutants were not predictable from the available pieces of data. Obtaining such antibody fragments with dual specificity and high affinity for the two gangliosides was possible because of the rational design of the phage display library, which combined a tailored soft randomization procedure with a careful selection of the positions to be mutated, based on structural knowledge, aiming to concentrate the sequence diversity of the library into the region of the antibody binding site that is relevant for binding of the ganglioside antigen.

Selection of scFv Fragments with Dual Specificity

The antibody fragments with dual specificity for the N-glycolyl GM3 and N-acetyl GM3 gangliosides, being the subject of the present invention, were obtained from the constructed library after three phage selection and amplification rounds using only the N-acetyl GM3 as target molecule, since a test single selection round with N-glycolyl GM3 demonstrated that the library contains a large number of fragments able to recognize this antigen.

The selection rounds were performed following a procedure similar to that described by Rojas and coworkers (J Immunol Methods 293:71-83, 2004). Exponentially growing TG1 cells were used to rescue the selected phages at a 50 ml scale, as described in (Marks et al., J Mol Biol 222:581-97, 1991). The purified phages were used as the starting material for the next selection round. After three rounds, individually selected phage clones were rescued in 96-well plates (Marks et al., J Mol Biol 222:581-97, 1991).

The capability of the selected phages to recognize N-acetyl GM3 and N-glycolyl GM3 was evaluated by ELISA following a procedure similar to that described in (Rojas et al., J Immunol Methods 293:71-83, 2004). The nucleotide sequences of those antibody fragments showing high binding capability to both gangliosides were determined by Macrogen (Korea).

Characterization of the Binding Site of the Antibodies with Dual Specificity

In addition to the fragments with dual specificity for NeuAc-GM3 and NeuGc-GM3, other antibody fragments derived from the library were also sequenced. This includes fragments that recognized only the N-glycolyl GM3, as well as fragments that were not able to recognize any of the two gangliosides in ELISA experiments.

Furthermore, the influence on binding of a selected group of amino acid positions was studied by performing an exhaustive randomization of each individual position, starting from one of the fragments with dual specificity.

These studies allowed determining which amino acids in the binding site are the most important for dual recognition of N-glycolyl GM3 and N-acetyl GM3. Table 1 shows a group of amino acid sequences of VH CDRs belonging to scFv fragments with dual specificity, extracted from the library. Table 2 shows which sequence positions in the VH domain are relevant for the dual specificity, and which positions admit different degrees of amino acid variability.

Only two or three mutations in CDR H1 were enough to confer to the fragments the capability of binding also to N-acetyl GM3, in addition to N-glycolyl GM3. In particular, the substitutions Ser 28→Arg, Thr 30→Arg and Trp 33→Gln produced a mutant (RRQ) with high affinity for both gangliosides.

Construction of Recombinant Immunoglobulins with Dual Specificity for the N-Acetyl GM3 and N-Glycolyl GM3 Gangliosides The present invention comprises immunoglobulins of any isotype, whether of human or murine origin, or from any other species, as well as any type of fragment of these immunoglobulins, which have dual specificity for the N-acetyl GM3 and N-glycolyl GM3 gangliosides. An immunoglobulin of any desired isotype can be constructed from the amino acid sequence of the VH domain of a scFv fragment with the capability to bind both gangliosides and a VL sequence of human or murine origin, or from any other species. This goal can be achieved employing established molecular biology techniques, using any of the vectors that have been described for efficient expression of recombinant proteins, in particular monoclonal antibodies.

In one embodiment, it is possible to construct an IgG1 isotype immunoglobulin using the vectors pAH4604 y pAG4622 (Coloma et al., J Immunol Methods 52:89-104, 1992), commonly used for the expression of immunoglobulin in mammalian cells.

The VH sequence to be used to construct an immunoglobulin with dual specificity can be extracted directly from the phage display library constructed in the present invention, or can be designed based on the experimental data shown in Table 1, maintaining in the sequence the positions that are important to achieve the dual specificity and introducing any other proper amino acid in the CDR positions that allow some degree of variability. The VL sequence to be used admits a large degree of variability, both in the framework and the hyper variable regions, as demonstrated in (Rojas et al., J Immunol Methods 293:71-83, 2004).

In another embodiment, the present invention provides also chimeric immunoglobulins, i.e. immunoglobulins with human constant regions and mouse variable regions, as well as immunoglobulins with humanized variable regions.

Pharmaceutical Compositions

In one embodiment, the invention provides pharmaceutical compositions that comprise one or more antibodies of the present invention, or their fragments. In one embodiment, these pharmaceutical compositions comprise also a pharmaceutically acceptable excipient.

As used in the present invention, the expression "Pharmaceutically acceptable carrier or adjuvant" comprise solvents, dispersion media, coatings, antibacterial and antifungal agents, isotonic and absorption delaying, and the like, compatible with pharmaceutical administration. Supplementary active compounds can also be incorporated into the compositions. "Pharmaceutically acceptable carrier or adjuvant" also refers to a carrier or adjuvant that can be administered to a subject, along with the antibodies or fragments, and which does not destroy the pharmacological activity thereof and is nontoxic when administered in doses sufficient to deliver a therapeutic amount of the antibody.

A pharmaceutical composition is formulated to be compatible with its intended route of administration. Examples of parenteral administration include, among others, for example, parenteral, intradermal, intravenous and subcutaneous. Solutions or suspensions used for parenteral, intradermal, or subcutaneous administration can include the following components: a sterile diluent such as water for injection, saline solution, fixed oils, polyethylene glycols, glycerine, propylene glycol or other synthetic solvents, antibacterial agents such as alcohol benzyl or methyl paraben, antioxidants such as ascorbic acid or sodium bisulfite; chelating agents such as ethylenediaminetetraacetic acid, buffers such as acetates, citrates or phosphates and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

It is advantageous to formulate parenteral compositions in dosage unit form for ease of administration and uniformity of dosage. The unit dosage form as used herein refers to physically discrete units suitable as unitary dosages for the subject to be treated, each unit containing a predetermined quantity of active compound calculated to produce the desired therapeutic effect, in association with the vehicle required pharmaceutical.

The pharmaceutical compositions can be included in a container, pack or dispenser together with instructions for administration.

Methods of Treatment

The antibodies of the present invention can be used for the treatment of tumors expressing either N-glycolyl GM3 or N-acetyl GM3, or both gangliosides.

A suitable therapeutic dose of the antibodies of the present invention is within a range from approximately 1 mg to approximately 1 gram per dose, preferably from approximately 50 mg to approximately 500 mg per dose. The antibodies of the invention are administered by any suitable way, including the parenteral, subcutaneous, intrapulmonary, intranasal and intracranial routes and, if desired for local treatment, the intralesional route.

A method of treatment comprises the administration of the pharmaceutical composition to the patient following a dose scheme that is suitable for passive therapy with monoclonal antibodies or derived fragments, as known to those skilled in the subject. An example of method of treatment, which does not limit the scope of the present invention, comprises the weekly administration of a 200 mg dose of an antibody of the invention during, for example, 6 weeks and a subsequent maintenance treatment, for example, every 2 or 3 weeks until disease progression or limiting toxicity.

EXAMPLES

Example 1

Construction of a Recombinant IgG1 Immunoglobulin (the 7C1 Antibody) with Dual Specificity for the N-Acetyl GM3 and N-Glycolyl GM3 Gangliosides A VH gene was designed taking as starting point the amino acid sequence of the VH domain from a scFv fragment with dual specificity for the N-acetyl GM3 and N-glycolyl GM3 gangliosides. This gene was optimized for expression in mammalian cells. A gene coding for the original VL domain of mAb 14F7 was designed in a similar way. The two genes were synthesized by Geneart (Germany).

The selected VH domain displays only three mutations at the amino acid level with respect to the original 14F7 VH sequence. These mutations are: Ser 28→Arg, Thr 30→Arg and Trp 33→Gln.

The genes coding for VH and VL were cloned into vectors pAH4604 and pAG4622 (Coloma et al., J Immunol Methods 52:89-104, 1992), respectively, following known molecular biology procedures. These vectors are used for the expression of immunoglobulins in mammalian cells. The pAH4604 vector contains a human heavy chain constant region of the IgG1 isotype, whereas the pAG4622 vector contains the constant domain of a human kappa chain. Sp2/0 mouse myeloma cells, which do not produce antibodies, were used to express the recombinant immunoglobulin. For this purpose the cells were sequentially transfected with the genetic constructions obtained for the heavy and light chains. The immunoglobulins produced by these cells were purified using a protein A column.

The obtained recombinant antibody was called as 7C1.

Figure 1:
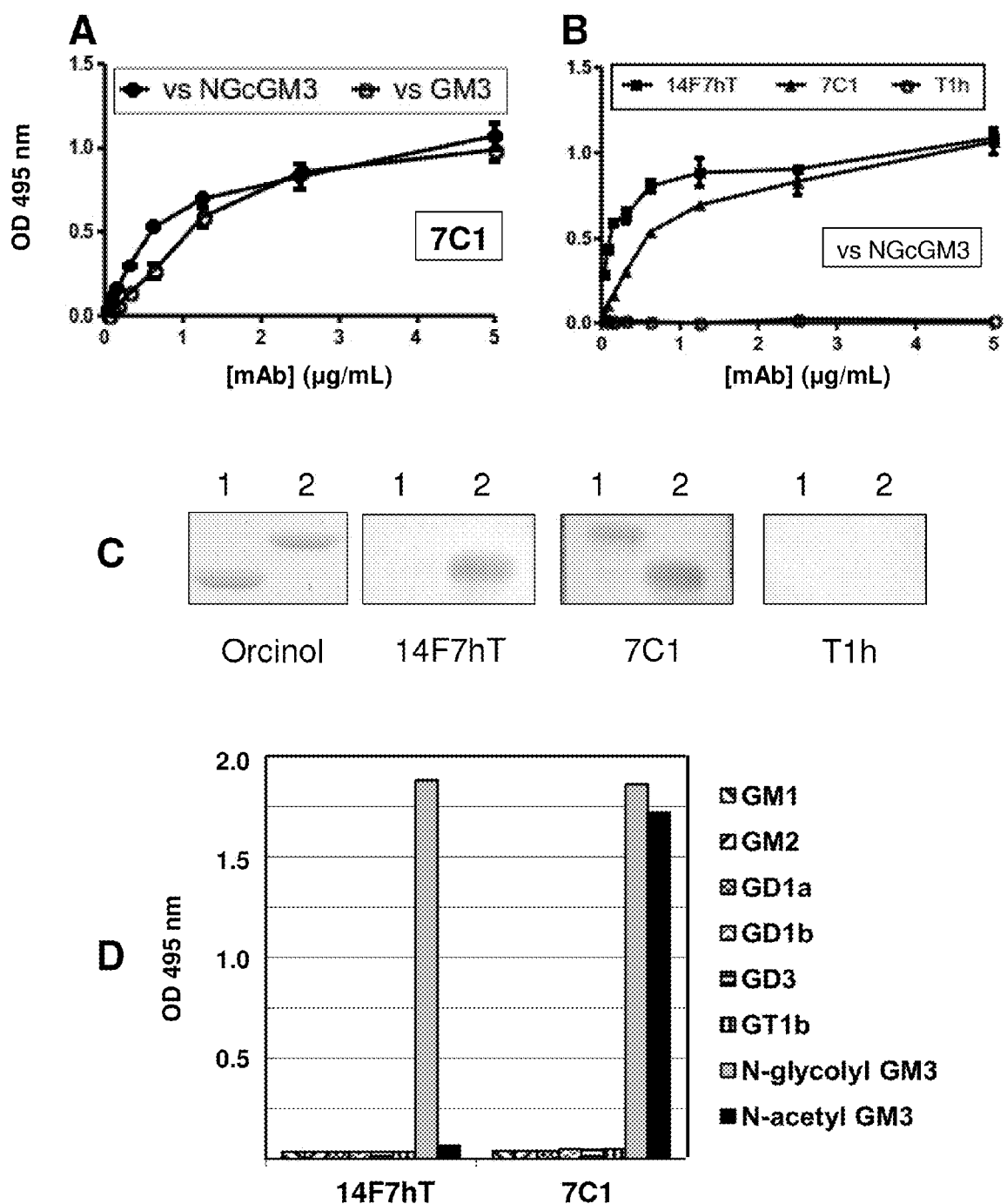
FIG. 1. A) Recognition of gangliosides N-glycolyl GM3 and N-acetyl GM3 by mAb 7C1 in ELISA experiments using different antibody concentrations. B) Recognition of the N-glycolyl GM3 ganglioside by the antibodies 14F7hT (humanized version of mAb 14F7 with a human IgG1 isotype), 7C1 and T1h (humanized antibody with human IgG1 isotype, used as negative control) in ELISA experiments. C) Immunostaining on TLC plates of the N-acetyl GM3 and N-glycolyl GM3 gangliosides (lanes 1 and 2, respectively, on each of the four plates). From left to right: chemical staining with orcinol and immunostaining with the antibodies 14F7hT, 7C1 and T1h, respectively. Only the 7C1 antibody showed reactivity with N-acetyl GM3. D) Recognition of a panel of different gangliosides by the antibodies 14F7hT and 7C1 in ELISA experiments.

The capability of mAb 7C1 to recognize the N-acetyl GM3 and N-glycolyl GM3 gangliosides was assessed by ELISA using different antibody concentrations, following a procedure similar to that described in (Rojas et al., J Immunol Methods 293:71-83, 2004). mAb 7C1 was capable of binding to both gangliosides practically with the same affinity, as demonstrated in FIG. 1A, showing that the two optical density (OD) curves that quantify antibody binding to the two gangliosides are very similar to each other. Furthermore, the affinity of the binding between mAb 7C1 and N-glycolyl GM3 (and, by transition, also between mAb 7C1 and N-acetyl GM3) is very similar to the affinity observed for the binding of mAb 14F7 to N-glycolyl GM3, as shown in FIG. 1B.

These experiments were carried out using a humanized version of mAb 14F7 with a human IgG1 isotype, called 14F7hT, which retains the binding properties of the original 14F7 antibody (Fernandez-Marrero et al., Immunobiology 216:1239-47, 2011). The antibody T1h (anti-CD6), having also a human IgG1 isotype, was used as negative control.

In addition, the capability of mAb 7C1 to bind to both gangliosides was proved by thin layer chromatography (TLC). mAb 7C1 was able to stain the bands yielded by purified samples of N-acetyl GM3 and N-glycolyl GM3, as shown in FIG. 1C.

The specificity of mAb 7C1 is truly dual, not multiple, as demonstrated in FIG. 1D, showing that the antibody did not recognize any of the molecules from a diverse panel that included gangliosides of both the N-acetyl and N-glycolyl types.

Example 2

Recognition by mAb 7C1 of Tumor Cell Lines Expressing N-Acetyl GM3 or N-Glycolyl GM3

The capability of mAb 7C1 to recognize tumor cells expressing either N-glycolyl GM3 or N-acetyl GM3 was demonstrated by flow cytometry using two variants of the L1210 mouse lymphocytic leukemia cell line (from the American Type Culture Collection). The wild type cells (L1210) express the N-glycolyl GM3, whereas a genetically transformed version called L1210-SH expresses the N-acetyl GM3 (Fernández-Marrero et al., Mol Immunol 48:1059-67, 2011).

The high N-glycolyl GM3 expression level of the L1210 is evidenced by the marked recognition of these cells by mAb 14F7. Furthermore, the analysis of the glycolipid contents of these cells yielded a 85:15 NeuGc-GM3/NeuAc-GM3 ratio. (Roque-Navarro et al., Mol Cancer Ther 7:2033-41, 2008).

The L1210-SH cell line, which expresses N-acetyl GM3 in place of the N-glycolyl variant, was obtained by lentiviral transduction of a short interference RNA that inhibits the expression of the CMP-NeuAc hydroxylase, which transforms the N-acetyl type of sialic acid into the N-glycolyl type (Shaw and Schauer, Biol Chem Hoppe Seyler 369:477-86, 1988). This transformed cell line shows a dramatic decrease in N-glycolyl GM3 expression, as compared with the wild type line (Fernández-Marrero et al., Mol Immunol 48:1059-67, 2011).

Flow cytometry experiments were carried out using a FACScan equipment (Becton Dickinson). $10^4$ cells were collected in each assay. A FITC-conjugated anti-human IgG antibody was used for fluorescence staining of cells. The T1h antibody was used as negative control.

Figure 2:
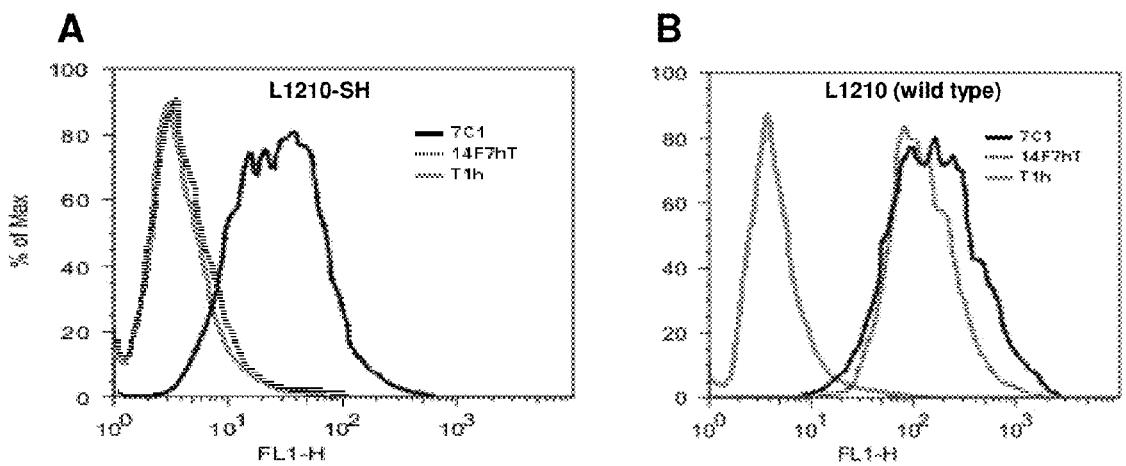
FIG. 2. Recognition by mAb 7C1 of tumor cell lines expressing N-acetyl GM3 or N-glycolyl GM3, in flow cytometry experiments. A) Staining of the transformed tumor cell line L1210-SH, which expresses only the N-acetyl variant of the GM3 ganglioside. B) Staining of the wild type tumor cell line L1210, which expresses mainly the N-glycolyl GM3 ganglioside.

As shown in FIG. 2A, mAb 7C1 was able to stain the L1210-SH cells (expressing N-acetyl GM3), in contrast to mAb 14F7hT, which does not recognize these cells. Furthermore, mAb 7C1 stained also the wild type L1210 cells, which have a high expression of N-glycolyl GM3. Wild type cells were stained also by mAb 14F7hT, used in this case as positive control (FIG. 2B). It should be noted that the staining of wild type L1210 cells by mAb 7C1 was stronger than the staining produced by mAb 14F7hT, which can be explained by the fact that mAb 7C1 can bind also to the N-acetyl GM3 molecules expressed in wild type cells.

Example 3

Cytotoxic Effect of mAb 7C1 on Tumor Cells Expressing N-Acetyl GM3 or N-Glycolyl GM3

The capability of mAb 7C1 to kill tumor cells expressing N-acetyl GM3 or N-glycolyl GM3 by a complement-independent mechanism was demonstrated in experiments using the L1210 and L1210-SH cell lines.

In these experiments the cells were first suspended in culture medium with 1% fetal bovine serum at 1 million cells/milliliter concentration, and then incubated with 100 microgram/milliliter of the antibody in a 5% $CO_2$ atmosphere at 37° C. for 3 hours. Afterwards the cells were washed, suspended in PBS with 10 microgram/milliliter propidium iodide (PI, Sigma-Aldrich), and then analyzed by flow cytometry. Dead cells were identified by measuring the frontal and lateral scattering and PI internalization. Cells with scattering levels outside the characteristic range of live cells and stained with PI were counted as dead.

Figure 3:
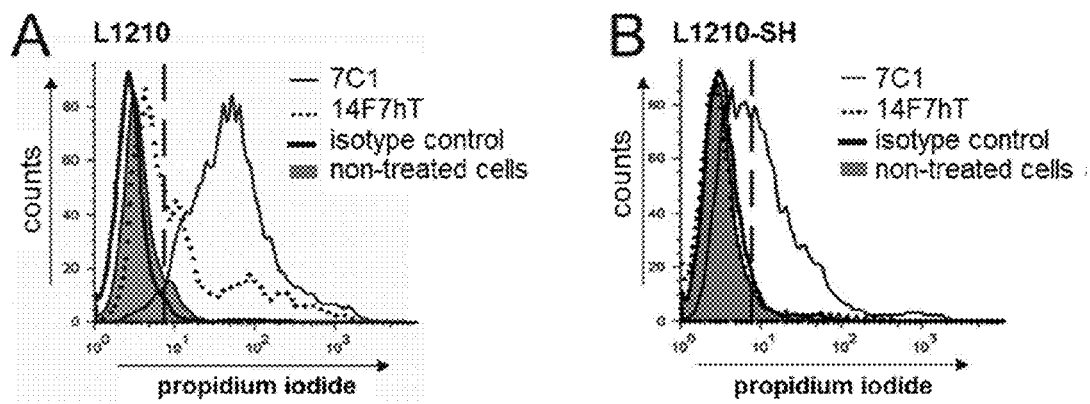
FIG. 3. Cytotoxic effect of the 7C1 antibody on tumor cells expressing either N-acetyl GM3 or N-glycolyl GM3, in comparison with the antibody 14F7hT. A) Cytotoxic effect on the wild type cell line L1210. B) Cytotoxic effect on the transformed cell line L1210-SH. C) Table summarizing the results from the experiments.

By difference with mAb 14F7hT, which produced cell death only in wild type L1210 cells, the antibody 7C1 with dual specificity produced a marked cell death effect both in the wild type L1210 cell line (FIG. 3A) and in the transformed L1210-SH cells expressing N-acetyl GM3 (FIG. 3B). It should be noted that the cytotoxic effect produced by the 7C1 antibody on wild type L1210 cells (95%) was stronger than that produced by mAb 14F7hT (54%), which demonstrates that mAb 7C1 can produce a stronger cytotoxic effect on cells having a mixed over-expression of the N-acetyl GM3 and N-glycolyl GM3 gangliosides. FIG. 3C summarizes the results from these experiments.

Example 4

Recognition of Normal Cells by mAb 7C1 without Producing Cell Death

The dual-specific 7C1 antibody, which produces a strong cytotoxic effect in tumor cells, did not produce, however, cell death in normal cells expressing N-glycolyl GM3 or N-acetyl GM3, as demonstrated in experiments using Balb/c mouse splenocytes.

In flow cytometry experiments, Balb/c mouse lymphocytes were double-stained with an anti-B220 polyclonal antibody (Dako, 1:200 dilution) and with mAb 7C1 (at a 10 microgram/milliliter concentration). Cell viability assays were performed using Balb/c spleen B lymphocytes, which were incubated with mAb 7C1. 1 million B lymphocytes, purified with magnetic pearls (Miltenyi Biotec), were incubated with 50 micrograms of antibody dissolved in DMEM-F12 medium supplemented with 1% BSA for 3 hours at 37° C. in a 5% $CO_2$ atmosphere. The antibody-induced cell death was determined by PI incorporation. The humanized antibody C5Q was used as negative control both in the cell recognition experiments and in the cell viability assays.

Figure 4:
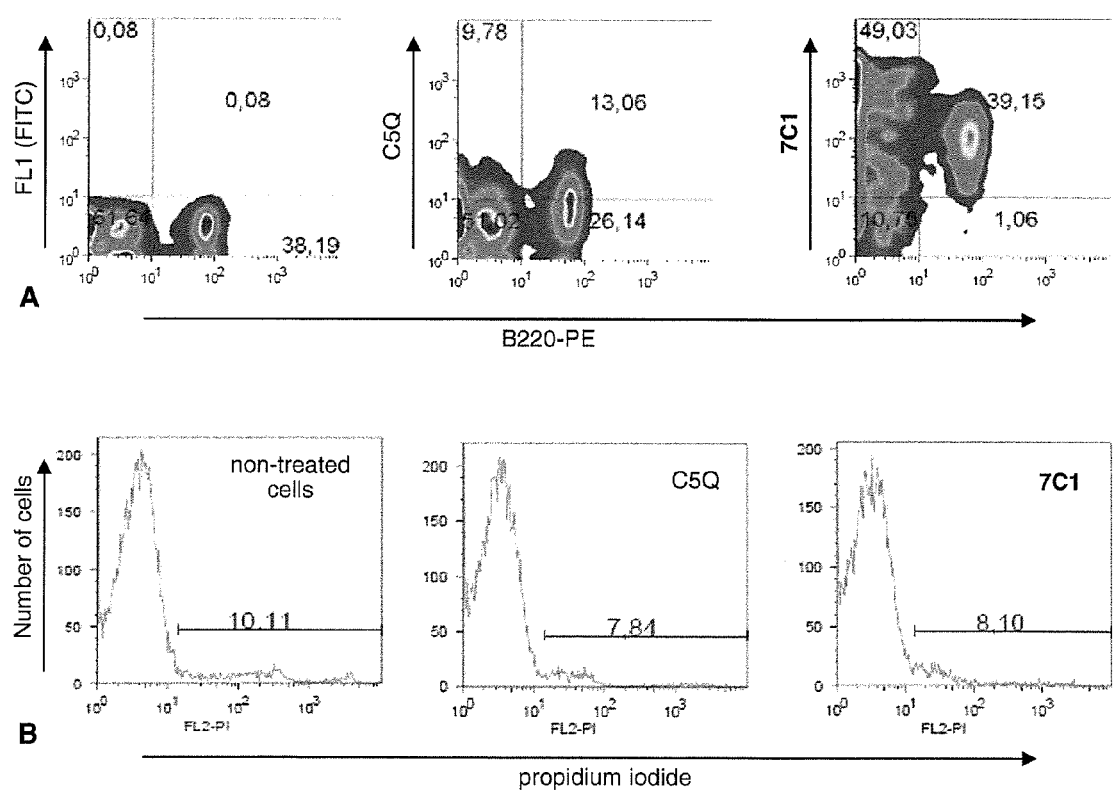
FIG. 4. A) Recognition of Balb/c mouse splenocytes by the humanized 7C1 antibody, in flow cytometry experiments. B) Cell viability assays using purified B lymphocytes from Balb/c mice, which were treated with the antibody 7C1. In both experiments, the B lymphocytes were stained with anti-B220 policlonal antibodies. The chimeric antibody C5Q was used as negative control.

As shown in FIG. 4A, mAb 7C1 strongly stained the Balb/c B lymphocytes, as well as other splenocytes. But in spite of the strong recognition of these cells by mAb 7C1, the cell viability assays with purified B lymphocytes demonstrated that mAb 7C1 has no cytotoxic effect on normal B lymphocytes, as shown in FIG. 4B.

TABLE 1

Sequences of the heavy chain hypervariable regions (CDRs) of scFv fragments, extracted from the phage display library, with dual specificity for the N-acetyl GM3 and N- glycolyl GM3 gangliosides.

| scFv don | CDR H1 * | CDR H2 | CDR H3 |
|---|---|---|---|
| 14F7 mAb (anti NeuGc-GM3) | GYSFTSYWIH | YIDPATAYTESNQKFKD | ESPRLRRGIYYYAMDY |
| 1 | --R-R--Q-- | ----------------- | ---------------- |
| 2 | -----R-Q-- | --N----S--------- | ---------------- |
| 3 | --R---NQ-- | F---------------- | ---------------- |
| 4 | ----NR-Q-- | D---GR----------- | ---------------- |
| 5 | ----RR-Q-- | -------N--------- | ---------------- |
| 6 | ---I-R-Q-- | --N----S--------- | ----F----------- |

TABLE 1-continued

Sequences of the heavy chain hypervariable regions (CDRs) of scFv fragments, extracted from the phage display library, with dual specificity for the N-acetyl GM3 and N- glycolyl GM3 gangliosides.

| scFv don | CDR H1 * | CDR H2 | CDR H3 |
|---|---|---|---|
| 7 | ----K--Q-- | F-N------------- | ---------------- |
| 8 | -----R-Q-- | -------N--------- | ---------------- |
| 9 | -----R-Q-- | F----S---V------- | ---------------- |
| 10 | -------Q-- | --N----S--------- | ---------------- |
| 11 | -----R-Q-- | -------K--------- | ---------------- |
| 12 | -----R-Q-- | ----------------- | --------R------- |
| 13 | -----R-Q-- | --N-GS----------- | ----M----------- |
| 14 | --R--R---- | -L---N----------- | ----V----------- |
| 15 | --R--R---- | -V---N----------- | ----V----------- |
| 16 | -----R-Q-- | --N-------------- | ---------------- |
| 17 | ----NR-Q-- | -------W--------- | ---------------- |
| 18 | --T--R-Q-- | ----G------------ | ---------------- |
| 19 | --P--R-Q-- | ----R------------ | --------L------- |
| 20 | ----SR-QV- | -V-----H--------- | --------L------- |
| 21 | --H----Q-- | --N-------------- | ---------------- |
| 22 | -----R-Q-- | --N------D------- | --------L------- |

* CDR H1 in the table includes positions 26-35 of the VH domain, according to (Chothia and Lesk, J Mol Biol 196: 901-17, 1987). Dashes in the sequences stand for amino acid identity with the corresponding amino acid in the sequence of mAb 14F7. The most frequent mutations are marked with bold letters.

TABLA 2

Effect on scFv binding to NeuAc-GM3 and NeuGc-GM3 of different amino acid substitutions made for a group of VH positions.

| Position | Original amino acid | Substitutions compatible with dual specificity * | Substitutions having negative effect on NeuAc-GM3 / NeuGc-GM3 binding |
|---|---|---|---|
| 33 | W | Q | C, E, G, H, K, N, P, R, S, T |
| 52 | D | A, E, N, S, T | C, F, H, K, P, R, V, Y |
| 53 | A | D, E, G, H, L, S, T, Y | C |
| 98 | R | R | A, E, G, I, K, L, M, N, P, Q, S, T, V, W, Y |
| 100-100A | RR | AK, HR, TR | GC, LD, PA, TD, AL, DR, LS, PQ, PT, TP, WP |
| 100B | G | A, D, F, L, Q, R, S | C |
| 100D | Y | F | D, G, H, K, L, P, Q, R, S, T, V |

* The substitutions that resulted compatible with dual specificity were made on the sequence of the RRQ mutant (the three letters stand for the amino acids present at positions 28, 30 and 33, respectively).

The invention claimed is:

1. A monoclonal antibody having dual specificity and high affinity for the N-acetyl GM3 and N-glycolyl GM3 gangliosides, wherein the antibody comprises the human IgG1 heavy chain constant region, and wherein the heavy chain variable region contains the following CDRs:

CDR-H1: GYRFRSYQIH,     SEQ ID NO: 3

CDR-H2: YIDPATAYTESNQKFKD,     SEQ ID NO: 17
    and

CDR-H3: ESPRLRRGIYYYAMDY,     SEQ ID NO: 34 and wherein the sequence of the light chain variable region is SEQ ID NO. 2.

2. A monoclonal antibody having dual specificity and high affinity for N-acetyl GM3 and N-glycolyl GM3 gangliosides, wherein the sequence of the heavy chain variable region is SEQ ID NO 1, and wherein the sequence of the light chain variable region is SEQ ID NO. 2, and wherein the antibody comprises the human IgG1 heavy chain constant region.

3. A monoclonal antibody having dual specificity and high affinity for N-acetyl GM3 and N-glycolyl GM3 gangliosides, characterized in that said antibody comprises the human IgG1 heavy chain constant region and wherein the sequence of the light chain variable region of said antibody is SEQ ID NO. 2 and said antibody comprises at least one sequence for CDR H1 selected from the group consisting of the following sequences:

CDR-H1 GYRFRSYQIH,     SEQ ID NO: 3

CDR-H1 GYSFTRYQIH,     SEQ ID NO: 4

CDR-H1 GYRFTSNQIH,     SEQ ID NO: 5

CDR-H1 GYSFNRYQIH,     SEQ ID NO: 6

CDR-H1 GYSFRRYQIH,     SEQ ID NO: 7

CDR-H1 GYSITRYQIH,     SEQ ID NO: 8

CDR-H1 GYSFTRYQIH,     SEQ ID NO: 9

CDR-H1 GYSFKSYQIH,     SEQ ID NO: 10

CDR-H1 GYSFTSYQIH,     SEQ ID NO: 11

CDR-H1 GYRFTRYWIH,     SEQ ID NO: 12

CDR-H1 GYTFTRYQIH,     SEQ ID NO: 13

CDR-H1 GYPFTRYQIH,     SEQ ID NO: 14

CDR-H1 GYSFSRYQIV,     SEQ ID NO: 15
    and

CDR-H1 GYHFTRYQIH,     SEQ ID NO: 16 and at least one sequence for CDR H2 selected from the group consisting of:

CDR-H2 YIDPATAYTESNQKFKD,     SEQ ID NO: 17

CDR-H2 YINPATASTESNQKFKD,     SEQ ID NO: 18

CDR-H2 FIDPATAYTESNQKFKD,     SEQ ID NO: 19

CDR-H2 DIDPGRAYTESNQKFKD,     SEQ ID NO: 20

CDR-H2 YIDPATANTESNQKFKD,     SEQ ID NO: 21

CDR-H2 FINPATAYTESNQKFKD,     SEQ ID NO: 22

CDR-H2 FIDPASAYTVSNQKFKD,     SEQ ID NO: 23

CDR-H2 YIDPATAKTESNQKFKD,     SEQ ID NO: 24

CDR-H2 YINPGSAYTESNQKFKD,     SEQ ID NO: 25

CDR-H2 YLDPANAYTESNQKFKD,     SEQ ID NO: 26

CDR-H2 YVDPANAYTESNQKFKD,     SEQ ID NO: 27

CDR-H2 YINPATAYTESNQKFKD,     SEQ ID NO: 28

CDR-H2 YIDPATAWTESNQKFKD,     SEQ ID NO: 29

CDR-H2 YIDPGTAYTESNQKFKD,     SEQ ID NO: 30

-continued

```
                               SEQ ID NO: 31
CDR-H2  YIDPRTAYTESNQKFKD,

SEQ ID NO: 32
CDR-H2  YVDPATAHTESNQKFKD,
and

SEQ ID NO: 33
CDR-H2  YINPATAYTDSNQKFKD,
``` and at least one sequence for CDR H3 selected from the group consisting of:

```
                               SEQ ID NO: 34
CDR-H3  ESPRLRRGIYYYAMDY,

SEQ ID NO: 35
CDR-H3  ESPRFRRGRYYYAMDY,

SEQ ID NO: 36
CDR-H3  ESPRMRRGIYYYAMDY,

SEQ ID NO: 37
CDR-H3  ESPRVRRGIYYYAMDY,
and

SEQ ID NO: 38
CDR-H3  ESPRLRRGLYYYAMDY.
```

4. A monoclonal antibody having dual specificity and high affinity for the N-acetyl GM3 and N-glycolyl GM3 gangliosides, wherein said antibody comprises the human IgG1 heavy chain constant region, wherein the heavy chain variable region contains the following CDRs:

```
    CDR-H1:   GYRFRSYQIH,         SEQ ID NO: 3

CDR-H2:   YIDPATAYTESNQKFKD,  SEQ ID NO: 17
    and

CDR-H3:   ESPRLRRGIYYYAMDY,   SEQ ID NO: 34;
``` and comprising at least one of the amino acid substitutions selected from the group consisting of:
- CDR-H2 Asp 52 substituted by Ala, Glu, Asn, Ser or Thr
- CDR-H2 Ala 53 substituted by Asp, Glu, Gly, His, Leu, Ser, Thr or Tyr
- CDR-H3 Arg 100-Arg 100A substituted by Ala-Lys, His-Arg or Thr-Arg
- CDR-H3 Gly 100B substituted by Ala, Asp, Phe, Leu, Gln, Arg or Ser and CDR-H3 Tyr 100 D substituted by Phe, and wherein the sequence of the light chain variable region is SEQ ID NO. 2.

5. An antibody fragment having dual specificity and high affinity for the N-acetyl GM3 and N-glycolyl GM3 gangliosides, and having a heavy chain variable region and a light chain variable region, wherein the heavy chain variable region comprises at least one sequence for CDR H1 selected from the group consisting of the following sequences:

```
                           SEQ ID NO: 3
CDR-H1  GYRFRSYQIH,

SEQ ID NO: 4
CDR-H1  GYSFTRYQIH,

SEQ ID NO: 5
CDR-H1  GYRFTSNQIH,

SEQ ID NO: 6
CDR-H1  GYSFNRYQIH,

SEQ ID NO: 7
CDR-H1  GYSFRRYQIH,

SEQ ID NO: 8
CDR-H1  GYSITRYQIH,

SEQ ID NO: 9
CDR-H1  GYSFTRYQIH,

SEQ ID NO: 10
CDR-H1  GYSFKSYQIH,

SEQ ID NO: 11
CDR-H1  GYSFTSYQIH,

SEQ ID NO: 12
CDR-H1  GYRFTRYWIH,

SEQ ID NO: 13
CDR-H1  GYTFTRYQIH,

SEQ ID NO: 14
CDR-H1  GYPFTRYQIH,

SEQ ID NO: 15
CDR-H1  GYSFSRYQIV,
and

SEQ ID NO: 16
CDR-H1  GYHFTRYQIH,
``` and at least one sequence for CDR H2 selected from the group consisting of:

```
                              SEQ ID NO: 17
CDR-H2  YIDPATAYTESNQKFKD,

SEQ ID NO: 18
CDR-H2  YINPATASTESNQKFKD,

SEQ ID NO: 19
CDR-H2  FIDPATAYTESNQKFKD,

SEQ ID NO: 20
CDR-H2  DIDPGRAYTESNQKFKD,

SEQ ID NO: 21
CDR-H2  YIDPATANTESNQKFKD,

SEQ ID NO: 22
CDR-H2  FINPATAYTESNQKFKD,

SEQ ID NO: 23
CDR-H2  FIDPASAYTVSNQKFKD,

SEQ ID NO: 24
CDR-H2  YIDPATAKTESNQKFKD,

SEQ ID NO: 25
CDR-H2  YINPGSAYTESNQKFKD,

SEQ ID NO: 26
CDR-H2  YLDPANAYTESNQKFKD,

SEQ ID NO: 27
CDR-H2  YVDPANAYTESNQKFKD,

SEQ ID NO: 28
CDR-H2  YINPATAYTESNQKFKD,

SEQ ID NO: 29
CDR-H2  YIDPATAWTESNQKFKD,

SEQ ID NO: 30
CDR-H2  YIDPGTAYTESNQKFKD,
```

```
                                        SEQ ID NO: 31
CDR-H2  YIDPRTAYTESNQKFKD,

SEQ ID NO: 32
CDR-H2  YVDPATAHTESNQKFKD,
and

SEQ ID NO: 33
CDR-H2  YINPATAYTDSNQKFKD,
``` and at least one sequence for CDR H3 selected from the group consisting of:

```
                                        SEQ ID NO: 34
CDR-H3  ESPRLRRGIYYYAMDY,

SEQ ID NO: 35
CDR-H3  ESPRFRRGRYYYAMDY,

SEQ ID NO: 36
CDR-H3  ESPRMRRGIYYYAMDY,

SEQ ID NO: 37
CDR-H3  ESPRVRRGIYYYAMDY,
and

SEQ ID NO: 38
CDR-H3  ESPRLRRGLYYYAMDY.
```

6. The fragment according to claim 5, characterized in that said fragment is of the Fab type.

7. The fragment according to claim 5, characterized in that said fragment is of the Fab' type.

8. The fragment according to claim 5, characterized in that said fragment is of the (Fab)2 type.

9. The fragment according to claim 5, characterized in that said fragment is of the scFv type.

10. A pharmaceutical composition for the treatment of malignant tumors expressing the N-acetyl GM3 and/or the N-glycolyl GM3 gangliosides, characterized in that said pharmaceutical composition comprises at least one antibody of claim 1, and a stable pharmaceutical vehicle.

11. A kit of reagents for the diagnosis of diseases that express the N-acetyl GM3 and/or the N-glycolyl GM3 gangliosides, characterized in that said kit of reagents comprises at least one antibody of claim 1.

12. A pharmaceutical composition for the treatment of malignant tumors expressing the N-acetyl GM3 and/or the N-glycolyl GM3 gangliosides, characterized in that said pharmaceutical composition comprises at least one antibody of claim 2 and a stable pharmaceutical vehicle.

13. A pharmaceutical composition for the treatment of malignant tumors expressing the N-acetyl GM3 and/or the N-glycolyl GM3 gangliosides, characterized in that said pharmaceutical composition comprises at least one antibody of claim 3 and a stable pharmaceutical vehicle.

14. A pharmaceutical composition for the treatment of malignant tumors expressing the N-acetyl GM3 and/or the N-glycolyl GM3 gangliosides, characterized in that said pharmaceutical composition comprises at least one antibody of claim 4 and a stable pharmaceutical vehicle.

15. A pharmaceutical composition for the treatment of malignant tumors expressing the N-acetyl GM3 and/or the N-glycolyl GM3 gangliosides, characterized in that said pharmaceutical composition comprises at least one antibody fragment of claim 5 and a stable pharmaceutical vehicle.

16. A kit of reagents for the diagnosis of diseases that express the N-acetyl GM3 and/or the N-glycolyl GM3 gangliosides, characterized in that said kit of reagents comprises at least one antibody of claim 2.

17. A kit of reagents for the diagnosis of diseases that express the N-acetyl GM3 and/or the N-glycolyl GM3 gangliosides, characterized in that said kit of reagents comprises at least one antibody of claim 3.

18. A kit of reagents for the diagnosis of diseases that express the N-acetyl GM3 and/or the N-glycolyl GM3 gangliosides, characterized in that said kit of reagents comprises at least one antibody of claim 4.

19. A kit of reagents for the diagnosis of diseases that express the N-acetyl GM3 and/or the N-glycolyl GM3 gangliosides, characterized in that said kit of reagents comprises at least one antibody fragment of claim 5.

20. The fragment according to claim 5, wherein the light chain variable region is murine.

\* \* \* \* \*

SEQUENCE LISTING

<160> NUMBER OF SEQ ID NOS: 38

<210> SEQ ID NO 1
<211> LENGTH: 125
<212> TYPE: PRT
<213> ORGANISM: Artifical Sequence
<220> FEATURE:

<223> OTHER INFORMATION: recombinant

<400> SEQUENCE: 1

Gln Val Gln Leu Gln Gln Ser Gly Asn Glu Leu Ala Lys Pro Gly Ala
1               5                   10                  15

Ser Met Lys Met Ser Cys Arg Ala Ser Gly Tyr Arg Phe Arg Ser Tyr
            20                  25                  30

Gln Ile His Trp Leu Lys Gln Arg Pro Asp Gln Gly Leu Glu Trp Ile
        35                  40                  45

Gly Tyr Ile Asp Pro Ala Thr Ala Tyr Thr Glu Ser Asn Gln Lys Phe
    50                  55                  60

Lys Asp Lys Ala Ile Leu Thr Ala Asp Arg Ser Ser Asn Thr Ala Phe
65                  70                  75                  80

Met Tyr Leu Asn Ser Leu Thr Ser Glu Asp Ser Ala Val Tyr Tyr Cys
                85                  90                  95

Ala Arg Glu Ser Pro Arg Leu Arg Arg Gly Ile Tyr Tyr Ala Met
            100                 105                 110

Asp Tyr Trp Gly Gln Gly Thr Ser Val Thr Val Ser Ser
            115                 120                 125

<210> SEQ ID NO 2
<211> LENGTH: 109
<212> TYPE: PRT
<213> ORGANISM: Artifical Sequence
<220> FEATURE:
<223> OTHER INFORMATION: recombinant

<400> SEQUENCE: 2

Asp Leu Val Leu Thr Gln Ser Pro Ala Thr Leu Ser Val Thr Pro Gly
1               5                   10                  15

Asp Ser Val Ser Phe Ser Cys Arg Ala Ser Gln Ser Ile Ser Asn Asn
            20                  25                  30

Leu His Trp Tyr Gln Gln Arg Thr His Glu Ser Pro Arg Leu Leu Ile
        35                  40                  45

Lys Tyr Ala Ser Gln Ser Ile Ser Gly Ile Pro Ser Arg Phe Ser Gly
    50                  55                  60

Ser Gly Ser Gly Thr Asp Phe Thr Leu Ser Ile Ile Ser Val Glu Thr
65                  70                  75                  80

Glu Asp Phe Gly Met Tyr Phe Cys Gln Gln Ser Asn Arg Trp Pro Leu
                85                  90                  95

Thr Phe Gly Ala Gly Thr Lys Leu Glu Leu Lys Arg Ala
            100                 105

<210> SEQ ID NO 3
<211> LENGTH: 10
<212> TYPE: PRT
<213> ORGANISM: Artifical Sequence
<220> FEATURE:
<223> OTHER INFORMATION: recombinant

<400> SEQUENCE: 3

Gly Tyr Arg Phe Arg Ser Tyr Gln Ile His
1               5                   10

<210> SEQ ID NO 4
<211> LENGTH: 10
<212> TYPE: PRT
<213> ORGANISM: Artifical Sequence
<220> FEATURE:
<223> OTHER INFORMATION: recombinant

```
<400> SEQUENCE: 4

Gly Tyr Ser Phe Thr Arg Tyr Gln Ile His
1               5                   10

<210> SEQ ID NO 5
<211> LENGTH: 10
<212> TYPE: PRT
<213> ORGANISM: Artifical Sequence
<220> FEATURE:
<223> OTHER INFORMATION: recombinant

<400> SEQUENCE: 5

Gly Tyr Arg Phe Thr Ser Asn Gln Ile His
1               5                   10

<210> SEQ ID NO 6
<211> LENGTH: 10
<212> TYPE: PRT
<213> ORGANISM: Artifical Sequence
<220> FEATURE:
<223> OTHER INFORMATION: recombinant

<400> SEQUENCE: 6

Gly Tyr Ser Phe Asn Arg Tyr Gln Ile His
1               5                   10

<210> SEQ ID NO 7
<211> LENGTH: 10
<212> TYPE: PRT
<213> ORGANISM: Artifical Sequence
<220> FEATURE:
<223> OTHER INFORMATION: recombinant

<400> SEQUENCE: 7

Gly Tyr Ser Phe Arg Arg Tyr Gln Ile His
1               5                   10

<210> SEQ ID NO 8
<211> LENGTH: 10
<212> TYPE: PRT
<213> ORGANISM: Artifical Sequence
<220> FEATURE:
<223> OTHER INFORMATION: recombinant

<400> SEQUENCE: 8

Gly Tyr Ser Ile Thr Arg Tyr Gln Ile His
1               5                   10

<210> SEQ ID NO 9
<211> LENGTH: 10
<212> TYPE: PRT
<213> ORGANISM: Artifical Sequence
<220> FEATURE:
<223> OTHER INFORMATION: recombinant

<400> SEQUENCE: 9

Gly Tyr Ser Phe Thr Arg Tyr Gln Ile His
1               5                   10

<210> SEQ ID NO 10
<211> LENGTH: 10
<212> TYPE: PRT
<213> ORGANISM: Artifical Sequence
<220> FEATURE:
<223> OTHER INFORMATION: recombinant
```

```
<400> SEQUENCE: 10

Gly Tyr Ser Phe Lys Ser Tyr Gln Ile His
1               5                   10

<210> SEQ ID NO 11
<211> LENGTH: 10
<212> TYPE: PRT
<213> ORGANISM: Artifical Sequence
<220> FEATURE:
<223> OTHER INFORMATION: recombinant

<400> SEQUENCE: 11

Gly Tyr Ser Phe Thr Ser Tyr Gln Ile His
1               5                   10

<210> SEQ ID NO 12
<211> LENGTH: 10
<212> TYPE: PRT
<213> ORGANISM: Artifical Sequence
<220> FEATURE:
<223> OTHER INFORMATION: recombinant

<400> SEQUENCE: 12

Gly Tyr Arg Phe Thr Arg Tyr Trp Ile His
1               5                   10

<210> SEQ ID NO 13
<211> LENGTH: 10
<212> TYPE: PRT
<213> ORGANISM: Artifical Sequence
<220> FEATURE:
<223> OTHER INFORMATION: recombinant

<400> SEQUENCE: 13

Gly Tyr Thr Phe Thr Arg Tyr Gln Ile His
1               5                   10

<210> SEQ ID NO 14
<211> LENGTH: 10
<212> TYPE: PRT
<213> ORGANISM: Artifical Sequence
<220> FEATURE:
<223> OTHER INFORMATION: recombinant

<400> SEQUENCE: 14

Gly Tyr Pro Phe Thr Arg Tyr Gln Ile His
1               5                   10

<210> SEQ ID NO 15
<211> LENGTH: 10
<212> TYPE: PRT
<213> ORGANISM: Artifical Sequence
<220> FEATURE:
<223> OTHER INFORMATION: recombinant

<400> SEQUENCE: 15

Gly Tyr Ser Phe Ser Arg Tyr Gln Ile Val
1               5                   10

<210> SEQ ID NO 16
<211> LENGTH: 10
<212> TYPE: PRT
<213> ORGANISM: Artifical Sequence
<220> FEATURE:
<223> OTHER INFORMATION: recombinant

<400> SEQUENCE: 16
```

```
Gly Tyr His Phe Thr Arg Tyr Gln Ile His
1               5                  10
```

<210> SEQ ID NO 17
<211> LENGTH: 17
<212> TYPE: PRT
<213> ORGANISM: Artifical Sequence
<220> FEATURE:
<223> OTHER INFORMATION: recombinant

<400> SEQUENCE: 17

```
Tyr Ile Asp Pro Ala Thr Ala Tyr Thr Glu Ser Asn Gln Lys Phe Lys
1               5                   10                  15

Asp
```

<210> SEQ ID NO 18
<211> LENGTH: 17
<212> TYPE: PRT
<213> ORGANISM: Artifical Sequence
<220> FEATURE:
<223> OTHER INFORMATION: recombinant

<400> SEQUENCE: 18

```
Tyr Ile Asn Pro Ala Thr Ala Ser Thr Glu Ser Asn Gln Lys Phe Lys
1               5                   10                  15

Asp
```

<210> SEQ ID NO 19
<211> LENGTH: 17
<212> TYPE: PRT
<213> ORGANISM: Artifical Sequence
<220> FEATURE:
<223> OTHER INFORMATION: recombinant

<400> SEQUENCE: 19

```
Phe Ile Asp Pro Ala Thr Ala Tyr Thr Glu Ser Asn Gln Lys Phe Lys
1               5                   10                  15

Asp
```

<210> SEQ ID NO 20
<211> LENGTH: 17
<212> TYPE: PRT
<213> ORGANISM: Artifical Sequence
<220> FEATURE:
<223> OTHER INFORMATION: recombinant

<400> SEQUENCE: 20

```
Asp Ile Asp Pro Gly Arg Ala Tyr Thr Glu Ser Asn Gln Lys Phe Lys
1               5                   10                  15

Asp
```

<210> SEQ ID NO 21
<211> LENGTH: 17
<212> TYPE: PRT
<213> ORGANISM: Artifical Sequence
<220> FEATURE:
<223> OTHER INFORMATION: recombinant

<400> SEQUENCE: 21

```
Tyr Ile Asp Pro Ala Thr Ala Asn Thr Glu Ser Asn Gln Lys Phe Lys
1               5                   10                  15

Asp
```

<210> SEQ ID NO 22
<211> LENGTH: 17
<212> TYPE: PRT
<213> ORGANISM: Artifical Sequence
<220> FEATURE:
<223> OTHER INFORMATION: recombinant

<400> SEQUENCE: 22

Phe Ile Asn Pro Ala Thr Ala Tyr Thr Glu Ser Asn Gln Lys Phe Lys
1               5                   10                  15
Asp

<210> SEQ ID NO 23
<211> LENGTH: 17
<212> TYPE: PRT
<213> ORGANISM: Artifical Sequence
<220> FEATURE:
<223> OTHER INFORMATION: recombinant

<400> SEQUENCE: 23

Phe Ile Asp Pro Ala Ser Ala Tyr Thr Val Ser Asn Gln Lys Phe Lys
1               5                   10                  15
Asp

<210> SEQ ID NO 24
<211> LENGTH: 17
<212> TYPE: PRT
<213> ORGANISM: Artifical Sequence
<220> FEATURE:
<223> OTHER INFORMATION: recombinant

<400> SEQUENCE: 24

Tyr Ile Asp Pro Ala Thr Ala Lys Thr Glu Ser Asn Gln Lys Phe Lys
1               5                   10                  15
Asp

<210> SEQ ID NO 25
<211> LENGTH: 17
<212> TYPE: PRT
<213> ORGANISM: Artifical Sequence
<220> FEATURE:
<223> OTHER INFORMATION: recombinant

<400> SEQUENCE: 25

Tyr Ile Asn Pro Gly Ser Ala Tyr Thr Glu Ser Asn Gln Lys Phe Lys
1               5                   10                  15
Asp

<210> SEQ ID NO 26
<211> LENGTH: 17
<212> TYPE: PRT
<213> ORGANISM: Artifical Sequence
<220> FEATURE:
<223> OTHER INFORMATION: recombinant

<400> SEQUENCE: 26

Tyr Leu Asp Pro Ala Asn Ala Tyr Thr Glu Ser Asn Gln Lys Phe Lys
1               5                   10                  15
Asp

<210> SEQ ID NO 27
<211> LENGTH: 17
<212> TYPE: PRT

```
<213> ORGANISM: Artifical Sequence
<220> FEATURE:
<223> OTHER INFORMATION: recombinant

<400> SEQUENCE: 27

Tyr Val Asp Pro Ala Asn Ala Tyr Thr Glu Ser Asn Gln Lys Phe Lys
1               5                   10                  15

Asp

<210> SEQ ID NO 28
<211> LENGTH: 17
<212> TYPE: PRT
<213> ORGANISM: Artifical Sequence
<220> FEATURE:
<223> OTHER INFORMATION: recombinant

<400> SEQUENCE: 28

Tyr Ile Asn Pro Ala Thr Ala Tyr Thr Glu Ser Asn Gln Lys Phe Lys
1               5                   10                  15

Asp

<210> SEQ ID NO 29
<211> LENGTH: 17
<212> TYPE: PRT
<213> ORGANISM: Artifical Sequence
<220> FEATURE:
<223> OTHER INFORMATION: recombinant

<400> SEQUENCE: 29

Tyr Ile Asp Pro Ala Thr Ala Trp Thr Glu Ser Asn Gln Lys Phe Lys
1               5                   10                  15

Asp

<210> SEQ ID NO 30
<211> LENGTH: 17
<212> TYPE: PRT
<213> ORGANISM: Artifical Sequence
<220> FEATURE:
<223> OTHER INFORMATION: recombinant

<400> SEQUENCE: 30

Tyr Ile Asp Pro Gly Thr Ala Tyr Thr Glu Ser Asn Gln Lys Phe Lys
1               5                   10                  15

Asp

<210> SEQ ID NO 31
<211> LENGTH: 17
<212> TYPE: PRT
<213> ORGANISM: Artifical Sequence
<220> FEATURE:
<223> OTHER INFORMATION: recombinant

<400> SEQUENCE: 31

Tyr Ile Asp Pro Arg Thr Ala Tyr Thr Glu Ser Asn Gln Lys Phe Lys
1               5                   10                  15

Asp

<210> SEQ ID NO 32
<211> LENGTH: 17
<212> TYPE: PRT
<213> ORGANISM: Artifical Sequence
<220> FEATURE:
<223> OTHER INFORMATION: recombinant
```

```
<400> SEQUENCE: 32

Tyr Val Asp Pro Ala Thr Ala His Thr Glu Ser Asn Gln Lys Phe Lys
1               5                  10                  15

Asp

<210> SEQ ID NO 33
<211> LENGTH: 17
<212> TYPE: PRT
<213> ORGANISM: Artifical Sequence
<220> FEATURE:
<223> OTHER INFORMATION: recombinant

<400> SEQUENCE: 33

Tyr Ile Asn Pro Ala Thr Ala Tyr Thr Asp Ser Asn Gln Lys Phe Lys
1               5                  10                  15

Asp

<210> SEQ ID NO 34
<211> LENGTH: 16
<212> TYPE: PRT
<213> ORGANISM: Artifical Sequence
<220> FEATURE:
<223> OTHER INFORMATION: recombinant

<400> SEQUENCE: 34

Glu Ser Pro Arg Leu Arg Arg Gly Ile Tyr Tyr Tyr Ala Met Asp Tyr
1               5                  10                  15

<210> SEQ ID NO 35
<211> LENGTH: 16
<212> TYPE: PRT
<213> ORGANISM: Artifical Sequence
<220> FEATURE:
<223> OTHER INFORMATION: recombinant

<400> SEQUENCE: 35

Glu Ser Pro Arg Phe Arg Arg Gly Arg Tyr Tyr Tyr Ala Met Asp Tyr
1               5                  10                  15

<210> SEQ ID NO 36
<211> LENGTH: 16
<212> TYPE: PRT
<213> ORGANISM: Artifical Sequence
<220> FEATURE:
<223> OTHER INFORMATION: recombinant

<400> SEQUENCE: 36

Glu Ser Pro Arg Met Arg Arg Gly Ile Tyr Tyr Tyr Ala Met Asp Tyr
1               5                  10                  15

<210> SEQ ID NO 37
<211> LENGTH: 16
<212> TYPE: PRT
<213> ORGANISM: Artifical Sequence
<220> FEATURE:
<223> OTHER INFORMATION: recombinant

<400> SEQUENCE: 37

Glu Ser Pro Arg Val Arg Arg Gly Ile Tyr Tyr Tyr Ala Met Asp Tyr
1               5                  10                  15

<210> SEQ ID NO 38
<211> LENGTH: 16
<212> TYPE: PRT
<213> ORGANISM: Artifical Sequence
```

<220> FEATURE:
<223> OTHER INFORMATION: recombinant

<400> SEQUENCE: 38

```
Glu Ser Pro Arg Leu Arg Arg Gly Leu Tyr Tyr Tyr Ala Met Asp Tyr
1               5                   10                  15
```